US008128947B2

(12) United States Patent
Jones et al.

(10) Patent No.: US 8,128,947 B2

(45) Date of Patent: Mar. 6, 2012

(54) SURFACTANT-FREE DISPERSIONS, COMPOSITIONS, AND USE IN TOPICAL FORMULATIONS

(75) Inventors: David P. Jones, San Antonio, TX (US); Duncan T. Aust, Fort Worth, TX (US); Vitthal Kulkarni, San Antonio, TX (US)

(73) Assignee: DPT Laboratories, Ltd., San Antonio, TX (US)

( * ) Notice: Subject to any disclaimer, the term of this patent is extended or adjusted under 35 U.S.C. 154(b) by 1168 days.

(21) Appl. No.: 11/548,537

(22) Filed: Oct. 11, 2006

(65) Prior Publication Data

US 2007/0104665 A1 May 10, 2007

Related U.S. Application Data

(60) Provisional application No. 60/725,373, filed on Oct. 11, 2005.

(51) Int. Cl.
*A61K 9/00* (2006.01)
*A61K 8/02* (2006.01)

(52) U.S. Cl. ........................................ 424/401; 424/400

(58) Field of Classification Search .................. 424/400, 424/401

See application file for complete search history.

(56) References Cited

U.S. PATENT DOCUMENTS 2,680,735 A 6/1954 Rowland ...................... 260/86.1
2,877,215 A 3/1959 Fang ........................... 260/86.1
2,967,173 A 1/1961 Fang et al. ................... 260/77.5
2,979,514 A 4/1961 Beavers et al. ............ 260/340.2
3,932,609 A * 1/1976 Rosenstreich et al. .......... 424/68
3,957,362 A 5/1976 Mancini et al. ............... 351/160
4,781,923 A 11/1988 Pellico .......................... 424/130
4,801,740 A 1/1989 Hammar ....................... 560/224
4,837,019 A 6/1989 Georgalas et al. ............ 424/101
4,863,725 A 9/1989 Deckner et al. ............ 514/772.4
5,043,155 A 8/1991 Puchalski et al. ............... 424/78
5,420,118 A 5/1995 Alban et al. .................... 514/63
5,476,662 A 12/1995 Narayanan et al. ........... 424/409
5,567,426 A 10/1996 Nadaud et al. ................ 424/401
5,576,064 A 11/1996 Fructus ......................... 424/401
5,653,982 A 8/1997 Spagnoli et al. .............. 424/401
5,656,278 A 8/1997 Enjolras ........................ 424/401
5,703,041 A 12/1997 Afriat et al. ....................... 514/2
5,833,951 A 11/1998 Artz et al. ....................... 424/47
5,869,075 A 2/1999 Krzysik ........................ 424/414
5,879,718 A 3/1999 Sebillote-Arnaud ......... 424/705
5,894,019 A 4/1999 Hesse et al. ................... 424/484
5,908,618 A 6/1999 Lorant .......................... 424/705
5,928,632 A * 7/1999 Reusch ...................... 424/78.03
6,074,986 A 6/2000 Mulqueen ..................... 504/116
6,106,848 A 8/2000 Preuilh ......................... 424/401
6,361,781 B2 3/2002 Lorant .......................... 424/401
6,403,109 B1 6/2002 Stora ............................ 424/401
6,485,756 B1 11/2002 Aust et al. ..................... 424/725
6,924,129 B2 8/2005 Gross et al. ................... 435/100
7,175,834 B2 2/2007 Aust et al. ....................... 424/59
2003/0026856 A1 2/2003 Aust et al. ...................... 424/725
2003/0215470 A1 11/2003 Wilmott et al. ............... 424/400
2003/0215471 A1* 11/2003 Wilmott et al. ............... 424/401
2003/0228267 A1 12/2003 Aust et al. ........................ 424/59
2004/0013698 A1 1/2004 Aust et al. ...................... 424/401
2004/0018250 A1 1/2004 Ceccoli et al. ................ 424/725
2004/0042991 A1 3/2004 Klug et al. ................. 424/70.12
2004/0109836 A1 6/2004 Loffler et al. .............. 424/70.12
2005/0019291 A1 1/2005 Zolotarsky et al. ........ 424/70.11
2006/0116524 A1 6/2006 Bruening et al. ............. 554/166
2006/0159716 A1 7/2006 Themens et al. .............. 424/401

FOREIGN PATENT DOCUMENTS

EP 0332501 9/1989
EP 0513183 11/1992
EP 0677287 10/1995
GB 2280605 2/1995
KR 2003-0051972 6/2003
WO WO 91/11171 8/1991
WO WO 94/08555 4/1994
WO WO 97/47310 12/1997
WO WO 00/68176 11/2000
WO WO 02/100523 12/2002
WO WO 2005/084631 9/2005

OTHER PUBLICATIONS

Barany et al., "Biophysical characterization of skin damage and recovery after exposure to different surfactants," *Contact Dermatitis*, 40:98-103, 1999.
Bodin et al., "Skin irritation from air-oxidized ethoxylated surfactants," *Contact Dermatitis*, 43:82-89, 2000.
Bovin, "Polyacrylamide-based glycoconjugates as tools in glycobiology," *Glycoconjugate J.*, 15:431-446, 1998.
Effendy & Maibach, "Surfactants and experimental irritant contact dermatitis," *Contact Dermatitis*, 33:217-225, 1995.
Gantrez Copolymers Technical Profile, *International Specialty Products*, 1999.
Gantrez Copolymers, *International Specialty Products*, http://www.ispcorp.com/products/housespec/content/brochure/hii/gantrez.html, 2005.
Granhydrogel GA Product Bulletin, *Grant Industries*, 2005.
Granhydrogel O Product Bulletin, *Grant Industries*, 2005.
Hispagel Oil Product Bulletin, *Centerchem, Inc.*, 2004.
Lubrajel Oil Sales Specifications, *International Specialty Products, Inc.*, 2001.
Lubrajel Product Bulletin, *Guardian Laboratories*.
Pashley, R.M., "Effect of Degassing on the Formation and Stability of Surfactant-Free Emulsions and Fine Teflon Dispersions", *J. Phys. Chem. B*, vol. 107, No. 7, 1714-1720, 2003.
Sahoo et al., "Regio- and stereoselective esterification of polyacrylic acid with glycerol using novozym 435 as the catalyst," *Polymeric Materials: Science & Engineering*, 91:529-530, 2004.
Wengst, J., Daniels, R., "Influence of a hydrophilic polymer on a polymer stabilized w/o emulsion", *Proc. International Meeting on Pharmaceutics, Biopharmaceutics, and Pharmaceutical Technology*, Nuremburg, Mar. 2004.

(Continued)

*Primary Examiner* — Johann Richter
*Assistant Examiner* — Luke Karpinski
(74) *Attorney, Agent, or Firm* — Fulbright & Jaworski L.L.P.

(57) ABSTRACT

The present invention provides for the preparation of stable surfactant-free dispersions of hydrophobic substances in low viscosity hydrophilic glyceryl polyacrylate or glyceryl polymethacrylate fluids, and topical vehicles formulated with the dispersions.

15 Claims, No Drawings

OTHER PUBLICATIONS

"PVM/MA Copolymer," International Cosmetic Ingredient Dictionary and Handbook, The Cosmetic, Toiletry and Fragrance Association (Gottschalck and McEwen, eds.), pp. 1589, 2004.

"Surfactants—Suspending Agents," International Cosmetic Ingredient Dictionary and Handbook, The Cosmetic, Toiletry and Fragrance Association (Gottschalck and McEwen, eds.), pp. 2290-2291, 2004.

"Suspending Agents—Nonsurfactant," International Cosmetic Ingredient Dictionary and Handbook, The Cosmetic, Toiletry and Fragrance Association (Gottschalck and McEwen, eds.), pp. 2291-2292, 2004.

PCT International Search Report and Written Opinion, dated Feb. 5, 2007.

* cited by examiner

SURFACTANT-FREE DISPERSIONS, COMPOSITIONS, AND USE IN TOPICAL FORMULATIONS

CROSS REFERENCE TO RELATED APPLICATION

This application claims the benefit of U.S. Provisional Application No. 60/725,373, filed Oct. 11, 2005, the contents of which are incorporated by reference.

BACKGROUND OF THE INVENTION

A. Field of the Invention

The present invention relates generally to the preparation of surfactant-free dispersions comprising a low viscosity hydrophilic continuous phase and the use of such dispersions in topical formulations. In certain aspects, the present invention is directed to stable surfactant-free dispersions of hydrophobic substances in low viscosity hydrophilic glyceryl polyacrylate or glyceryl polymethacrylate fluids, and topical vehicles formulated with such ingredients.

B. Background

Topical formulations generally have to combine multiple, and sometimes competing, attributes, such as those relating to aesthetics, stability, delivery and compatibility. In regard to aesthetics, topical formulations are generally required to display appropriate tactile and visual properties when applied to the skin. Such formulations should also maintain functionality in regard to the delivery of various active agents onto or into the skin. Stability requirements apply both to individual ingredients (e.g., active agents) as well as to more gross aspects of the product form, such as precipitation or potential separation of phases. Compatibility constraints generally require that a formulation can be applied to the skin without eliciting a significant adverse reaction, such as an allergic or irritant response.

Formulations range from aqueous based solutions and gels to anhydrous vehicles. Simple aqueous based vehicles have limitations in regard to both solubility and stability of active agents, and can have poor tactile properties. Anhydrous vehicles have limitations in regard to desirable aesthetic properties. Emulsions are often employed in skin formulations to obviate such problems. An emulsion is a dispersion comprising two immiscible liquid phases, wherein one phase, a non-continuous phase, is dispersed into the continuous phase. The two basic types of such dispersions usually comprise either a hydrophilic, e.g. aqueous, dispersed phase in a hydrophobic continuous phase (water-in-oil) or a hydrophobic dispersed phase in a hydrophilic continuous phase (oil-in-water).

Emulsions are generally made by preparing separate hydrophobic and hydrophilic phases and mixing the two together. This is generally accomplished with the use of one or more emulsifying agents which reduce the surface tension between the immiscible phases creating micelles, i.e., a surfactant effect, thereby making the dispersion physically stable. However, surfactants have long been known to be associated with skin irritation and comprise the majority of adverse skin reaction to personal care products (e.g., Barany et al., 1999; Bodin et al., 2000; Effendy & Maibach, 1995).

Low viscosity dispersions are advantageous in that they can be readily processed through various mixers, mills and homogenizing equipment in order to produce a stable dispersion without the build up of excessive heat, which can occur when processing high viscosity "gel-like" dispersions due to friction. Low viscosity dispersions can spread and absorb easily into the skin and impart a characteristic "light" feel. However, the omission of surfactants from low viscosity dispersions would be expected to result in physical instability of the dispersed phase, i.e. phase separation, in contrast to high viscosity dispersions wherein the gel-like consistency physically stabilizes the dispersed particles.

SUMMARY OF THE INVENTION

The present invention overcomes the deficiencies in the art by providing surfactant-free dispersions suitable for formulating topical preparations. The removal of surfactants will generally enhance cutaneous compatibility of topical preparations. For instance, skin irritation can be reduced or prevented. An additional benefit of the dispersions and compositions of the present invention is the reduction in manufacturing costs by excluding surfactants and detergents from the dispersions and compositions of the present invention.

In one aspect of the present invention, there is disclosed a dispersion comprising a hydrophobic dispersed phase in a hydrophilic fluid continuous phase. The hydrophilic continuous phase can include glyceryl polyacrylate or glyceryl polymethacrylate, or mixtures of the two. A unique aspect of the dispersion is that it is surfactant free and stable. Stated another way, no surfactants are needed to obtain a stable dispersion of the present invention. In certain embodiments, the dispersion comprises from about 30, 35, 40, 45, 50, 55, 60, 65, 70, 75, 80, 85, 90, 95 to about 99%, or any range or integer derivable therein, by weight of the glyceryl polyacrylate. In other aspects, the dispersion can include from about 30, 35, 40, 45, 50, 55, 60, 65, 70, 75, 80, 85, 90, 95 to about 99%, or any range or integer derivable therein, by weight of the glyceryl polymethacrylate. The viscosity of the hydrophilic fluid can range from about 20 to about 1600 cps. In certain aspects, the viscosity of the hydrophilic fluid is 20, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600 cps, or any range or integer derivable therein.

In certain aspects, the dispersion can include from about 15, 10, 15, 20, 25, 30, 35, 40, 45, 50, 55, 60, 65, 70, 75, 80, 85, 90, 95 to about 99%, or any range or integer derivable therein, by weight of the hydrophobic dispersed phase. The hydrophobic phase can include a plant, animal, paraffinic, or synthetic derived fat, butter, grease, solvent, wax, or oil, or mixtures thereof. The hydrophobic phase can include a non-volatile silicone, a mineral oil, a vegetable oil, a water insoluble organic ester, a water insoluble triglyceride, or a fluorinated compound, or mixtures thereof. In other embodiments, the hydrophobic dispersed phase can be a liquid and/or can have a melting point below 25° C. In other aspects, the melting point can be below 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 6° C., 5° C., 4° C., 3° C., 2° C., or 1° C. In certain aspects the hydrophobic dispersed phase does not include a wax.

The dispersion of the present invention can also include water, a polyol, or mixtures thereof. Non-limiting examples of polyols include glycerin, propylene glycol, butylene glycol, or pentylene glycol, or mixtures thereof. The dispersion can be incorporated into a vehicle. The vehicle can be a cosmetic or pharmaceutical vehicle. The vehicle can be formulated for topical application to skin. The vehicle can be a lotion, a cream, a gel, an ointment, a serum, a liquid, a fluid, a non-aerosol spray, an aerosol spray, a non-aerosol foam, or an aerosol foam. In certain embodiments, the dispersion is comprised in a cosmetic skin care product.

In another embodiment of the present invention, the inventors disclose a surfactant free topical vehicle that includes a dispersion of the present invention. By way of example, the topical vehicle can include a cosmetic ingredient, or a pharmaceutical active agent, or mixtures thereof. The term "cosmetic ingredient" includes, but is not limited to, "rheology modifiers" and "cosmetic active agents." Non-limiting examples of cosmetic ingredients include preservatives, colorants, fragrances, pH adjusters, antioxidants, chelating agents, absorbents, exfoliants, humectants, skin lightening agents, waterproofing agents, skin conditioning agents, or mixtures thereof. The topical vehicle can include a rheology modifier. Non-limiting examples of rheology modifiers include sodium polyacrylate, carbomer, natural gum, natural gum derivative, clay, modified clay, cellulose, cellulose derivative, magnesium aluminum silicate, gellan gum, xanthan gum, starch, and modified starch, or mixtures thereof. In certain non-limiting embodiments, the topical vehicle can be a lotion, cream, gel, ointment, serum, liquid, fluid, non-aerosol spray, aerosol spray, non-aerosol foam, or aerosol foam. The topical vehicle can have a pH of from about 3, 4, 5, 6, 7, 8, 9, 10 to about 11, or any range or integer derivable therein.

Also disclosed is a method of topically delivering a pharmaceutical or cosmetic ingredient to skin comprising contacting the skin of a subject (e.g., animals and humans or persons) with a topical vehicle of the present invention. The method can include applying the topical vehicle or compositions of the present invention to skin at least once, twice, three, four, five, six, seven, eight, nine, or more times a day as needed. In certain non-limiting aspects, the topical vehicle or compositions of the present invention can be incorporated into clothes, wound dressings, bandages, gauzes and the like.

Another aspect of the present invention includes a method of preparing a surfactant free topical vehicle. The method can include admixing a hydrophobic phase with a low viscosity hydrophilic phase comprising a glyceryl polyacrylate or glyceryl polymethacrylate fluid to obtain a stable dispersion. The stable dispersion can then be combined with an additional non-surfactant ingredient such as a cosmetic or pharmaceutical ingredient. The admixing can be performed by methods and apparatuses known to those of ordinary skill in the art including, but not limited to, mechanical mixers, mills, dispersers, and homogenizers.

It is contemplated that any embodiment discussed in this specification can be implemented with respect to any method or composition of the invention, and vice versa. Furthermore, compositions of the invention can be used to achieve methods of the invention.

The term "dispersion" refers to a suspension of liquid, semi-solid, or solid particles of colloidal size or larger in a liquid medium. In various embodiments, the particle size can range from about 50 nanometers to about 1000 microns. In typical embodiments, the suspended particles contain one or more hydrophobic materials.

The phrase "stable dispersion" means a dispersion that is physically stable by visual examination for at least about 5 days.

The term "fluid" means a low viscosity liquid. "Low viscosity" means a viscosity of from about 20 to about 1600 cps as measured by a BROOKFIELD RV model viscometer using a #3 spindle at 50 rpm at 25° C.

The use of the word "a" or "an" when used in conjunction with the term "comprising" in the claims and/or the specification may mean "one," but it is also consistent with the meaning of "one or more," "at least one," and "one or more than one."

Throughout this application, the terms "about" and "approximately" indicate that a value includes the inherent variation of error for the device, the method being employed to determine the value, or the variation that exists among the study subjects. In one non-limiting embodiment the terms are defined to be within 10%, preferably within 5%, more preferably within 1%, and most preferably within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

One aspect of the present invention provides for stable dispersions of hydrophobic substances in low viscosity hydrophilic glyceryl polyacrylate or glyceryl polymethacrylate fluids. Further aspects provide for the use of the stable dispersions of the invention in topical vehicles and methods of delivering pharmaceutical and cosmetic active agents in such topical vehicles. These and other aspects of the present invention are described in further detail below.

A. Surfactant Free Preparations

For the purposes of the present invention, the term "surfactants" means those compounds or mixture of compounds recognized by one of ordinary skill in the art as surfactants and emulsifiers useful in formulating topical preparations such as emulsions. Examples of such surfactants can be found in McCutcheon's Emulsifiers and Detergents (2001) under "Surfactants" and examples include, but are not limited to, the following (the CTFA/INCI name is denoted in parentheses for reference): block polymers, e.g., PLURONIC L44 (Poloxamer 124); ethoxylated alcohols e.g., BRIJ 52 (Ceteth-2), EUMULGIN B-2 (Ceteareth-20), GENAPOL 26-L3 (Laureth-3); ethoxylated fatty esters and oils, e.g., CREMOPHOR RH-40 (PEG-40 Hydrogenated Castor Oil), EMULSOGEN EL (PEG-36 Castor Oil), RITAPEG 150 DS (PEG-150 Distearate); glycerol esters, e.g., EMEREST 2452 (Polyglyceryl-3 Diisostearate), CREMOPHOR GS-11 (Glyceryl Stearate); glycol esters, ALKAMULS 600-DO (PEG-12 Dioleate), LEXEMUL P (Propylene Glycol Stearate SE); phosphate esters, e.g., HOSTAPHAT CC 100 (Cetyl Phosphate); polymeric surfactants, e.g., GANTREZ AN-119 (PVM/MA Copolymer), GANTREZ S-95 (PVM/MA Copolymer), PEMULIN TR-1 (Acrylates/C10-30 Alkyl Acrylate Crosspolymer), PEMULIN TR-2 (Acrylates/C10-30 Alkyl Acrylate Crosspolymer); quaternary surfactants, e.g., DEHYQUART A (Cetrimonium Chloride); Silicone Based Surfactants, e.g., ABIL B-88183 (PEG/PPG-20/6 Dimethicone); Sorbitan Derivatives, e.g., ARLACEL 60 (Sorbitan Stearate), TWEEN 60 (Polysorbate 60); sucrose and glucose esters and derivatives, e.g., GLUCAMATE SSE-20 (PEG-20 Methyl Glucose Sesquistearate); and sulfates of alcohols, e.g., STEPANOL WA-100 (Sodium Lauryl Sulfate). More generally, surfactants can be classified by their ionic type such as anionic, cationic, nonionic, or amphoteric. They can also be classified by their chemical structures, such as block polymers, ethoxylated alcohols, ethoxylated fatty esters and oils, glycerol esters, glycol esters, phosphate esters, polymeric surfactants, quaternary surfactants, silicone-based surfactants, sorbitan derivatives, sucrose and glucose esters and derivatives, and sulfates of alcohols. In that a formulation is "surfactant free," such surfactants are not included as ingredients.

B. Dispersion Phase Constituents

The stable dispersion of the present invention comprises a hydrophobic dispersed phase and a low viscosity hydrophilic glyceryl polyacrylate or glyceryl polymethacrylate continuous phase.

1. Hydrophilic Continuous Phase

A low viscosity glyceryl polyacrylate or glyceryl polymethacrylate fluid provides the hydrophilic continuous phase of the stable dispersions of the present invention. In some embodiments, the hydrophilic fluid further comprises water, a polyol, or mixtures thereof. In various embodiments, the polyol is glycerin, propylene glycol, butylene glycol, or pentylene glycol; or mixtures thereof. As noted above, "low viscosity" means a viscosity of from about 20 to about 1600 cps as measured by a BROOKFIELD RV model viscometer using a #3 spindle at 50 rpm at 25° C. In various embodiments, the viscosity of the hydrophilic fluid is from about 400 cps to about 1600 cps, or is from about 500 cps to about 1200 cps, or is about 400 cps, or is about 500 cps, or is about 600 cps, or about 700 cps, or about 800 cps, or about 900 cps, or about 1000 cps, or about 1100 cps, or about 1200 cps, or about 1300 cps, or about 1400 cps, or about 1500 cps, or is from about 20 cps to about 400 cps, or is from about 20 cps to about 500 cps, or is from about 20 cps to about 600 cps, or is from about 20 cps to about 700 cps, or is from about 20 cps to about 800 cps, or is from about 20 cps to about 900 cps, or is from about 20 cps to about 1000 cps, or is from about 20 cps to about 1100 cps, or is from about 20 cps to about 1200 cps, or is from about 20 cps to about 1300 cps, or is from about 20 cps to about 1400 cps, or is from about 20 cps to about 1500 cps.

A suitable commercially available glyceryl polyacrylate fluid is HISPAGEL Oil LV (manufactured by Cognis Iberia S.L., Spain and distributed by Centerchem, Inc., Norwalk, Conn.), which is a mixture of glyceryl polyacrylate, glycerin and water, and is supplied with a viscosity in the range of 500-1200 cps. HISPAGEL Oil LV does not contain surfactants. It should be noted that other commercially available materials such as LUBRAJEL Oil (manufactured by ISP Corp), GRANHYDROGEL 0 (manufactured by Grant Industries), and CREAGEL Oil (manufactured by Cosmetics Innovations and Technologies Sarl), which contain either glyceryl polyacrylate or glyceryl polymethacrylate, all include the commonly known surfactant PVM/MA Copolymer. Thus, formulations made with these materials would not be surfactant free.

Suitable glyceryl polyacrylate and glyceryl polymethacrylate preparations can be prepared by use of methods known in the art to esterify polyols to polyacids. Such methods include conventional chemical synthesis (e.g., U.S. Pat. No. 2,680,735; U.S. Pat. No. 2,877,215; U.S. Pat. No. 2,967,173, U.S. Pat. No. 2,979,514; Bovin, 1998, all incorporated herein by reference) and use of enzymes (e.g., Sahoo & Gross, 2004; U.S. Pat. No. 6,924,129, all incorporated herein by reference). Preparation of a suitable glyceryl polyacrylate fluid by use of NOVOZYME 435 (Lipase B from *Candida antartica*) is exemplified in Example 6 below. Preparation of a suitable glyceryl polymethacrylate fluid is exemplified in Example 8 below.

2. Hydrophobic Dispersed Phase

Suitable components of the hydrophobic dispersed phase include, but are not limited to plant, animal, paraffinic, and synthetic derived fats, butters, greases, waxes, solvents, and oils; mineral oils, vegetable oils, water insoluble organic esters, water insoluble triglycerides, non-volatile silicones, and fluorinated compounds; and mixtures thereof. Plant derived materials include, but are not limited to, arachis (peanut) oil, balsam Peru oil, carnauba wax, candelilla wax, castor oil, hydrogenated castor oil, cocoa butter, coconut oil, corn oil, cotton seed oil, jojoba oil, *macadamia* seed oil, olive oil, orange oil, orange wax, palm kernel oil, rapeseed oil, safflower oil, sesame seed oil, shea butter, soybean oil, sunflower seed oil, tea tree oil, vegetable oil, and hydrogenated vegetable oil. Non-limiting examples of animal derived materials include beeswax, cod liver oil, emu oil, lard, mink oil, shark liver oil, squalane, squalene, and tallow. Non-limiting examples of paraffinic materials include isoparaffin, microcrystalline wax, heavy mineral oil, light mineral oil, ozokerite, petrolatum, and paraffin. A non-limiting example of a non-volatile silicone is dimethicone. Suitable hydrophobic materials also include C12-15 alkyl benzoate, isopropyl myristate, isopropyl palmitate, trilaurin, trihydroxystearin, and polytetrafluoroethylene (PTFE).

In other embodiments, the hydrophobic dispersed phase can be a liquid and/or can have a melting point below 25° C. In certain aspects the hydrophobic dispersed phase does not include a wax.

C. Topical Formulations

The topical formulations of the present invention comprise the low viscosity surfactant free dispersion of the present invention and other suitable ingredients such as cosmetic ingredients and pharmaceutical active agents, including those known to persons of ordinary skill in the art and/or described throughout the specification. Topical formulations may be made by first preparing the low viscosity dispersion and subsequently adding the other ingredients of the topical formulations. Alternatively, one or more, or all the other ingredients of a topical formulation, may be added at the time the surfactant free dispersion of the present invention is made by admixing the appropriate phases.

Typically, the topical formulations of the present invention can be applied to the skin without undue toxicity, incompatibility, instability, allergic response, and the like. The term "cosmetic ingredients" includes "rheology modifiers" and "cosmetic active agents", i.e., agents directed to enhancing, modifying or maintaining a biological or physiological functionality other than those such agents required for prescribed or over-the-counter drugs, these being pharmaceutical active agents.

1. Cosmetic Ingredients

In regard to cosmetic ingredients generally, the CTFA International Cosmetic Ingredient Dictionary and Handbook (2004) describes a wide variety of non-limiting cosmetic ingredients commonly used in the skin care industry, generally suitable for use in the compositions of the present invention. Examples of these ingredient classes include: fragrances (artificial and natural), dyes and color ingredients (e.g., Blue 1, Blue 1 Lake, Red 40, and titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), and botanical extracts (e.g. aloe vera, chamomile, cucumber extract, *ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., glycerin, propylene glycol, butylene glycol, pentylene glycol, sorbitol, urea, and manitol), exfoliants (e.g., alpha-hydroxyacids, and beta-hydroxyacids such as lactic acid, glycolic acid, and salicylic acid; and salts thereof) waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

a. Preservatives

Non-limiting examples of preservatives that can be used in the context of the present invention include parabens (e.g., methylparabens and propylparabens), benzyl alcohol, chlorobutanol, phenol, sorbic acid, thimerosal or combinations thereof.

b. Moisturizers

Non-limiting examples of moisturizing agents that can be used with the compositions of the present invention can be found in the International Cosmetic Ingredient Dictionary, $10^{th}$ Ed., 2004, which is incorporated by reference. Examples include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, polyglyceryl sorbitol, salts of pyrollidone carboxylic acid, potassium PCA, propylene glycol, sodium glucuronate, sodium PCA, sorbitol, sucrose, trehalose, urea, and xylitol.

c. Emollients

Examples of emollients include, but are not limited to, vegetable oils, mineral oils, silicone oils, synthetic and natural waxes, medium chain triglycerides, petrolatum, lanolin, aluminum magnesium hydroxide stearate (which can also function as a water repellent), and fatty acid esters. Non-limiting examples of vegetable oils include safflower oil, corn oil, sunflower seed oil, and olive oil.

d. Antioxidants

Examples of antioxidants include, but are not limited to, acetyl cysteine, ascorbic acid, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

2. Pharmaceutical Active Agents

Pharmaceutical active agents may include, but are not limited to, anti-acne agents including those for the treatment of rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound debriding agents, wound treatment agents, wound healing agents, and retinoids including retinol, retinoic acid and retinoic acid derivatives.

3. Rheology Modifiers

Topical formulations of the invention may include rheology modifiers (also known as thickeners). Such agents used in topical formulations are known to those of skill in the art and serve to impart certain desirable physical attributes such as product consistency, texture, and viscosity to a formulation. Typically rheology modifiers may be selected from sodium polyacrylates, carbomers, natural gums, natural gum derivatives, clays, modified clays, cellulose, cellulose derivatives, magnesium aluminum silicates, gellan gums, xanthan gums, starches and modified starches. By selecting certain rheology modifiers or combinations of such, the formulator can achieve the desired physical characteristics of a topical formulation. Examples of rheology modifiers can be found in McCutcheon's Functional Materials (2001) under "Thickeners" and include the following (the CTFA/INCI name is denoted in parentheses for reference):

ALCOGUM (Sodium Polyacrylate) manufactured by Alco Chemical

AVICEL RC (Microcrystalline Cellulose & Cellulose Gum) manufactured by FMC

BENTOLITE WH (Bentonite) manufactured by Southern Clay Products

CARBOPOL 974P (Carbomer) manufactured by B.F. Goodrich/Noveon

KELCOGEL (Gellan Gum) manufactured by CP Kelco

KLUCEL (Hydroxypropylcellulose) manufactured by Hercules Inc.

NATROSOL (Hydroxyethylcellulose) manufactured by Hercules Inc.

RHODIGEL (Xanthan Gum) manufactured by R.T. Vanderbilt Co.

VEEGUM (Magnesium Aluminum Silicate) manufactured by R.T. Vanderbilt Co.

For the purpose of this invention, the selection of rheology modifiers and any additional topical vehicle ingredients should not include those materials that are also surfactants, as in the surfactant examples listed in McCutcheon's Emulsifiers and Detergents (2001) under "Surfactants."

In the foregoing products, it is important that the concentrations and combinations of the compounds and ingredients be selected in such a way that the combinations are chemically compatible and do not cause instability of the finished product.

D. Concentration Ranges of Ingredients

A person of ordinary skill will recognize that the compositions of the present invention can include any number of combinations of ingredients (components of the dispersions (e.g., the hydrophobic and hydrophilic phases), cosmetic ingredients, pharmaceutical active ingredients, etc.) of the present invention. It is also contemplated that the concentrations of these ingredients within the compositions can vary. In non-limiting embodiments, for example, the compositions may include in their final form, for example, at least about 0.0001% to about 0.001%, 0.001% to about 0.01%, 0.01% to about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

A person of ordinary skill in the art would also recognize that the selection of the concentrations and combinations of ingredients can be made in such a way that the combinations are chemically compatible and do not cause instability of the finished product.

E. Equivalents

Known and unknown equivalents to the ingredients discussed throughout this specification can be used with the dispersions, compositions, and methods of the present invention. The equivalents can be used as substitutes for the ingredients and/or can be added to the methods, dispersions, compositions of the present invention. A person of ordinary skill in the art would be able to recognize and identify acceptable known and unknown equivalents to the ingredients without undue experimentation.

F. Vehicles

The dispersions and compositions of the present invention can be incorporated into several different vehicles. Non-limiting examples of suitable vehicles include emulsions (e.g., water-in-oil, water-in-oil-in-water, oil-in-water, oil-in-water-in-oil, oil-in-water-in-silicone emulsions), creams, lotions, solutions (both aqueous and hydro-alcoholic), anhydrous bases (such as lipsticks and powders), gels, ointments, serums, liquids, fluids, non-aerosol sprays, aerosol sprays, non-aerosol foams, aerosol foams or by other method or any combination of the forgoing as would be known to one of ordinary skill in the art (Remington's, 1990). Variations and other appropriate vehicles will be apparent to the skilled artisan and are appropriate for use in the present invention. In certain aspects, it is important that the concentrations and combinations of ingredients be selected in such a way that the combinations are chemically compatible and do not form complexes which precipitate from the finished product.

G. Products

The dispersions and compositions of the present invention can also be used in many cosmetic and pharmaceutical products. Non-limiting examples of cosmetic products include sunscreen products, sunless skin tanning products, hair products, finger nail products, moisturizing creams, skin benefit creams and lotions, softeners, day lotions, foundations, night creams, lipsticks, cleansers, toners, masks, and other known cosmetic products and applications. Non-limiting examples of pharmaceutical products include anti-acne products, analgesic products, anesthetic products, anorectal products, antihistamine products, anti-inflammatory products, antibiotic products, antifungal products, antiviral products, antimicrobial products, anti-cancer products, scabicidal products, pediculicidal products, antineoplastic products, antiperspirants, antipruritic products, antipsoriatic products, antiseborrheic products, burn treatment products, cauterizing products, depigmenting products, depilatory products, diaper rash treatment products, hair growth products, hair growth retardant products, hemostatic products, keratolytic products, canker sore treatment products, cold sore treatment products, dental and periodontal treatment products, skin protectant/barrier products, steroidal products including hormonal and corticosteroidal products, sunburn treatment products, sunscreen products, transdermal products, nasal products, vaginal products, wart treatment products, wound debriding products, wound treatment products, wound healing products.

H. Kits

Kits are also contemplated as being used in certain aspects of the present invention. For instance, the dispersions or compositions of the present invention can be included in a kit. Containers can be included in the kit. Containers can include a bottle, a metal tube, a laminate tube, a plastic tube, a dispenser, a pressurized container, a barrier container, a package, a compartment, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the dispersion or composition. In other embodiments, the container can be squeezed (e.g., metal, laminate, or plastic tube) to dispense a desired amount of the dispersion or composition. The dispersion or composition can be dispensed as a spray, an aerosol, a liquid, a fluid, or a semi-solid. The containers can have spray, pump, or squeeze mechanisms. A kit can also include instructions for employing the kit components as well the use of any other dispersions or compositions included in the container. Instructions can include an explanation of how to apply, use, and maintain the products, dispersions, or compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Examples of Dispersions of the Present Invention

Non-limiting embodiments of dispersions of the present invention are described in the following Tables 1-6.

TABLE 1

(dispersion)*

| Ingredient | % w/w |
|---|---|
| HISPAGEL Oil LV | 85.7 |
| Mineral Oil USP | 14.3 |

*The dispersion was prepared as follows: The mineral oil was added to the HISPAGEL Oil while mixing with a COWLES disperser and mixed until uniform.

TABLE 2

(dispersion)*

| Ingredient | % w/w |
|---|---|
| HISPAGEL Oil LV | 62.5 |
| Mineral Oil USP | 37.5 |

*The dispersion was prepared as follows: The mineral oil was added to the HISPAGEL Oil while mixing with a COWLES disperser and mixed until uniform. The dispersion was passed through a GREECO Colloid Mill.

TABLE 3

(dispersion)*

| Ingredient | % w/w |
|---|---|
| HISPAGEL Oil LV | 50.0 |
| Mineral Oil USP | 50.0 |

*The dispersion was prepared as follows: The mineral oil was added to the HISPAGEL Oil while mixing with a COWLES disperser and mixed until uniform.

TABLE 4

(dispersion)*

| Ingredient | % w/w |
|---|---|
| HISPAGEL Oil LV | 68.0 |
| Mineral Oil USP | 32.0 |

*The dispersion was prepared as follows: The mineral oil was added to the HISPAGEL Oil while mixing with a COWLES disperser and mixed until uniform.

TABLE 5

(dispersion)*

| Ingredient | % w/w |
|---|---|
| HISPAGEL Oil LV | 62.6 |
| Safflower Oil USP | 37.4 |

*The dispersion was prepared as follows: The safflower oil was added to the HISPAGEL Oil while mixing with a COWLES disperser and mixed until uniform. The dispersion was passed through a GREECO Colloid Mill.

TABLE 6

(dispersion)*

| Ingredient | % w/w |
|---|---|
| HISPAGEL Oil LV | 62.5 |
| Caprylic/Capric Triglycerides | 37.5 |

*The dispersion was prepared as follows: The caprylic/capric triglycerides were added to the HISPAGEL Oil while mixing with a COWLES disperser and mixed until uniform.

Example 2

Example of a Surfactant Free Cream with Mineral Oil

A non-limiting example of a surfactant free cream with mineral oil was prepared as described in the following two steps:

Step 1: A mineral oil dispersion was prepared as described in Table 7 below:

TABLE 7

(mineral oil dispersion)*

| Ingredient | % w/w (of total surfactant free cream) |
|---|---|
| HISPAGEL Oil LV | 30.0 |
| Mineral Oil USP | 10.0 |

*The mineral oil was added to the HISPAGEL Oil while mixing with a COWLES disperser and mixed until uniform. The dispersion was passed through a GREECO Colloid Mill.

Step 2: The mineral oil dispersion was incorporated into an aqueous based topical vehicle as described in Table 8:

TABLE 8

(aqueous based topical vehicle)*

| Ingredient | % w/w |
|---|---|
| Xanthan Gum | 0.10 |
| Hydroxyethylcellulose | 0.10 |
| CARBOPOL 974P | 0.30 |
| Sodium Polyacrylate | 0.75 |
| Aluminum Starch Octenylsuccinate | 2.50 |
| Methylparaben | 0.25 |
| Propylparaben | 0.02 |
| Purified Water | q.s. ad 100% |
| Sodium Hydroxide | q.s. pH to 5-6 |

*The aqueous based topical vehicle was prepared by first dissolving the methylparaben and propylparaben in hot water then cooling the solution. The xanthan gum, hydroxytheylcellulose, CARBOPOL 974P, and sodium polyacrylate were then added and mixed with a COWLES disperser until hydrated. The aluminum starch octenylsuccinate was then added and mixed with a COWLES disperser. The Mineral Oil Dispersion was then blended with the vehicle using a mixer with a high lift impeller, and the pH was adjusted to 5-6 using sodium hydroxide.

Example 3

Example of a Surfactant Free Cream with Mineral Oil

An additional non-limiting example of a surfactant free cream with mineral oil was prepared as described in the following two steps:

Step 1: A mineral oil dispersion was prepared as described in Table 9 below:

TABLE 9

(mineral oil dispersion)*

| Ingredient | % w/w (of total surfactant free cream) |
|---|---|
| HISPAGEL Oil LV | 6.80 |
| Mineral Oil USP | 3.20 |

*The mineral oil was added to the HISPAGEL Oil while mixing with a COWLES disperser and mixed until uniform.

Step 2: The mineral oil dispersion was incorporated into an aqueous based topical vehicle as described in Table 10:

TABLE 10

(aqueous based topical vehicle)*

| Ingredient | % w/w |
|---|---|
| Xanthan Gum | 0.08 |
| Hydroxyethylcellulose | 0.16 |
| Sodium Polyacrylate | 1.33 |
| Methylparaben | 0.20 |
| Propylparaben | 0.03 |
| Purified Water | q.s. ad 100% |

*The aqueous based topical vehicle was prepared by first dissolving the methylparaben and propylparaben in hot water then cooling the solution. The sodium polyacrylate, hydroxytheylcellulose, and xanthan gum were then added and mixed with a COWLES disperser until hydrated. The mineral oil dispersion was then blended with the vehicle using a mixer with a 3-prong paddle blade and mixed until uniform.

Example 4

Example of a Surfactant Free Lotion with Mineral Oil

A non-limiting example of a surfactant free lotion with mineral oil was prepared as described in the following two steps:

Step 1: A mineral oil dispersion was prepared as described in Table 11 below:

TABLE 11

(mineral oil dispersion)*

| Ingredient | % w/w (of total surfactant free lotion) |
|---|---|
| HISPAGEL Oil LV | 27.2 |
| Mineral Oil USP | 12.8 |

*The mineral oil was added to the HISPAGEL Oil while mixing with a COWLES disperser and mixed until uniform. The dispersion was passed through a GREECO Colloid Mill.

Step 2: The mineral oil dispersion was incorporated into an aqueous based topical vehicle as described in Table 12:

TABLE 12

(aqueous based topical vehicle)*

| Ingredient | % w/w |
|---|---|
| Xanthan Gum | 0.10 |
| Hydroxyethylcellulose | 0.10 |
| Sorbitol Solution | 5.00 |
| Glycerin | 6.00 |
| Sodium Polyacrylate | 0.30 |
| Aluminum Starch Octenylsuccinate | 2.50 |
| Methylparaben | 0.20 |
| Propylparaben | 0.03 |
| Purified Water | q.s. ad 100% |

*The aqueous based topical vehicle was prepared by first dissolving the sorbitol solution in the water, then adding sodium polyacrylate and mixing until hydrated using a COWLES disperser. A solution of methylparaben and propylparaben in hot glyceryin was prepared, cooled, and then xanthan gum and hydroxyethyl cellulose were dispersed in theparaben solution. The paraben solution/xanthan gum/hydroxyethyl cellulose dispersion was then added to the batch and mixed with a COWLES disperser until uniform. The mineral oil dispersion was added to the vehicle while mixing with a paddle mixer and mixed until uniform. The aluminum starch octenylsuccinate was then added and mixed until uniform.

Example 5

Example of a Surfactant Free Lotion with Mineral Oil

An additional non-limiting example of a surfactant free lotion with mineral oil was prepared as described in the following two steps:

Step 1: A mineral oil dispersion was prepared as described in Table 13 below:

TABLE 13

(mineral oil dispersion)*

| Ingredient | % w/w (of total surfactant free lotion) |
|---|---|
| HISPAGEL Oil LV | 6.80 |
| Mineral Oil USP | 3.20 |

*The mineral oil was added to the HISPAGEL Oil while mixing with a COWLES disperser and mixed until uniform.

Step 2: The mineral oil dispersion was incorporated into an aqueous based topical vehicle as described in Table 14:

TABLE 14

(aqueous based topical vehicle)*

| Ingredient | % w/w |
|---|---|
| Xanthan Gum | 0.08 |
| Hydroxyethylcellulose | 0.10 |
| Sodium Polyacrylate | 0.40 |
| Methylparaben | 0.20 |
| Propylparaben | 0.03 |
| Purified Water | q.s. ad 100% |

*The aqueous based topical vehicle was prepared by first dissolving the methylparaben and propylparaben in hot water then cooling the solution. The sodium polyacrylate, hydroxytheylcellulose, and xanthan gum were then added and mixed with a COWLES disperser until hydrated. The mineral oil dispersion was then blended with the vehicle using a mixer with a 3-prong paddle blade and mixed until uniform.

Example 6

Synthesis of Glyceryl Polyacrylate Fluid

A non-limiting example of synthesizing glyceryl polyacrylate fluid is describe. The estrerification of the carboxylic groups of polyacrylic acid with glycerin generally followed the methodology of Sahoo & Gross, (2004), incorporated by reference. Polyacrylic acid (MW 750,000, Aldrich Chemicals) was suspended in glycerin along with the enzyme NOVOZYME 435 (Sigma Chemicals) as indicated in Table 15 below:

TABLE 15

| Ingredient | % w/w |
|---|---|
| Polyacrylic acid MW 750,000 | 1.0000 |
| Glycerin USP | 98.8336 |
| NOVOZYME 435 | 0.1664 |

The reaction was mixed for 6 consecutive days using a COWLES disperser at approximately 75° C. (the mixture was stored each night at room temperature without mixing). At the end of the reaction-mixing period, the enzyme beads were removed by centrifugation (the beads accumulate at the surface upon centrifugation). The fluid was completed by mixing 50% w/w of the reaction mixture with 50% w/w of 50:50 solution of water and glycerin using a COWLES disperser until a uniform fluid was formed. The viscosity of the fluid was 826 cps as measured by a BROOKFIELD RV model viscometer using a #3 spindle at 50 rpm at 25° C.

Example 7

Example of a Dispersion Having Glyceryl Polyacrylate Fluid as the Hydrophilic Phase A non-limiting example of a mineral oil dispersion having glyceryl polyacrylate fluid as the hydrophilic phase and mineral oil USP as the hydrophobic phase is described in Table 16 below. The glyceryl polyacrylate fluid was prepared as described in Example 6 and a dispersion was prepared as follows:

TABLE 16

(dispersion)*

| Ingredient | % w/w (of total surfactant free cream) |
|---|---|
| Glyceryl polyacrylate fluid (hydrophilic phase) | 76.7 |
| Mineral Oil USP (hydrophobic phase) | 23.3 |

*The hydrophobic phase was added to the hydrophilic phase and mixed with a COWLES disperser until homogeneous. The dispersion was physically stable by visual examination for at least 5 days.

Example 8

Synthesis of Glyceryl Polymethacrylate Fluid

A non-limiting example of synthesizing glyceryl polymethacrylate fluid is described. Suspend polymethacrylic acid in glycerin along with the enzyme NOVOZYME 435 (Sigma Chemicals). Mix the reaction using a COWLES disperser at approximately 70° C.-75° C. until the reaction is complete. At the end of the reaction-mixing period, remove the enzyme beads by centrifugation (the beads accumulate at the surface upon centrifugation). Complete the preparation of the fluid by mixing a portion of the reaction mixture with a portion of a solution of water and glycerin using a COWLES disperser until a uniform fluid is formed. Confirm the viscosity of the fluid is between 20 and 1600 cps as measured by a BROOKFIELD RV model viscometer using a #3 spindle at 50 rpm at 25° C.

Example 9

Example of a Dispersion Having Glyceryl Polymethacrylate Fluid as the Hydrophilic Phase A non-limiting example of a mineral oil dispersion having glyceryl polymethacrylate fluid as the hydrophilic phase and mineral oil USP as the hydrophobic phase is described in Table 17 below. The glyceryl polymethacrylate fluid is prepared as described in Example 8 and a dispersion is prepared as follows:

TABLE 17

(dispersion)*

| Ingredient | % w/w (of total surfactant free cream) |
|---|---|
| Glyceryl polymethacrylate fluid (hydrophilic phase) | 76.7 |
| Mineral Oil USP (hydrophobic phase) | 23.3 |

*The hydrophobic phase was added to the hydrophilic phase and mixed with a COWLES disperser until homogeneous. The dispersion was physically stable by visual examination for at least 5 days.

REFERENCES

The following references, to the extent that they provide exemplary procedural or other details supplementary to those set forth herein, are specifically incorporated herein by reference.

U.S. Pat. No. 2,680,735
U.S. Pat. No. 2,877,215
U.S. Pat. No. 2,967,173
U.S. Pat. No. 2,979,514
U.S. Pat. No. 6,924,129
Barany et al., *Contact Dermatitis,* 40:98, 1999.
Bodin et al., *Contact Dermatitis,* 43:82, 2000.
Bovin, *Glycoconjugate J.,* 15:431, 1998.
CTFA International Cosmetic Ingredient Dictionary and Handbook, Tenth Edition, 2004.
Effendy & Maibach, *Contact Dermatitis,* 33:217, 1995.
*McCutcheon's Emulsifiers and Detergents, North American Edition, Annual,* 2001.
Remington's Pharmaceutical Sciences, 18th Ed. Mack Printing Company, pp. 1289-1329, 1990.
Sahoo & Gross, *Polymeric Materials: Sci. & Eng.,* 91:529, 2004.

The invention claimed is:

1. A dispersion comprising:
a hydrophobic dispersed phase; and
30% to 90% by weight of a hydrophilic continuous phase having a viscosity ranging from 400 to 1600 cps comprising:
water;
glyceryl polyacrylate or glyceryl polymethacrylate; and a polyol,
wherein said dispersion is surfactant free and stable.

2. The dispersion of claim 1, wherein the viscosity of the hydrophilic continuous phase is from about 500 cps to about 1200 cps.

3. The dispersion of claim 1, wherein the hydrophobic dispersed phase comprises a plant, animal, paraffinic, or synthetic derived fat, butter, grease, solvent, wax, or oil, or mixtures thereof.

4. The dispersion of claim 1, wherein the hydrophobic phase comprises a non-volatile silicone, a mineral oil, a vegetable oil, a water insoluble organic ester, a water insoluble triglyceride, or a fluorinated compound, or mixtures thereof.

5. The dispersion of claim 1, wherein the polyol is glycerin, propylene glycol, butylene glycol, or pentylene glycol, or mixtures thereof.

6. The dispersion of claim 1, wherein the dispersion is incorporated into a cosmetic composition.

7. The dispersion of claim 6, wherein the cosmetic composition is formulated into a lotion, a cream, a gel, an ointment, a serum, a liquid, a fluid, a non-aerosol spray, an aerosol spray, a non-aerosol foam, or an aerosol foam.

8. A surfactant free topical vehicle comprising the dispersion of claim 1.

9. The topical vehicle of claim 8, further comprising a cosmetic ingredient, or a pharmaceutical active agent, or mixtures thereof.

10. The topical vehicle of claim 9, wherein the vehicle comprises a cosmetic ingredient.

11. The topical vehicle of claim 10, wherein said cosmetic ingredient is a preservative, a colorant, a fragrance, a pH adjuster, an antioxidant, a chelating agent, an absorbent, an exfoliant, a humectant, a skin lightening agent, a waterproofing agent, or a skin conditioning agent, or mixtures thereof.

12. The topical vehicle of claim 8, wherein the topical vehicle further comprises a rheology modifier.

13. The topical vehicle of claim 12 wherein the rheology modifier is selected from the group consisting of sodium polyacrylate, carbomer, natural gum, natural gum derivative, clay, modified clay, cellulose, cellulose derivative, magnesium aluminum silicate, gellant gum, xanthan gum, starch, and modified starch, or mixtures thereof.

14. The topical vehicle of claim 8, wherein said topical vehicle is a lotion, cream, gel, ointment, serum, liquid, fluid, non-aerosol spray, aerosol spray, non-aerosol foam, or aerosol foam.

15. A method of topically delivering a pharmaceutical or cosmetic active agent to skin comprising contacting the skin of a subject with a topical vehicle of claim 8.

* * * * *